(12) United States Patent
Chono et al.

(10) Patent No.: US 9,237,881 B2
(45) Date of Patent: Jan. 19, 2016

(54) ULTRASONIC DIAGNOSTIC APPARATUS AND METHOD OF RETRIEVING AND DISPLAYING HEART FUNCTION TEST PERIOD

(75) Inventors: Tomoaki Chono, Tokyo (JP); Osamu Mori, Tokyo (JP); Syunya Fukunaga, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 80 days.

(21) Appl. No.: 13/818,316

(22) PCT Filed: Aug. 25, 2011

(86) PCT No.: PCT/JP2011/069115
§ 371 (c)(1),
(2), (4) Date: Feb. 22, 2013

(87) PCT Pub. No.: WO2012/029616
PCT Pub. Date: Mar. 8, 2012

(65) Prior Publication Data
US 2013/0158399 A1    Jun. 20, 2013

(30) Foreign Application Priority Data
Aug. 31, 2010    (JP) .................................. 2010-193311

(51) Int. Cl.
*A61B 8/08*    (2006.01)
*A61B 8/02*    (2006.01)
(Continued)

(52) U.S. Cl.
CPC ... *A61B 8/52* (2013.01); *A61B 8/02* (2013.01); *A61B 8/0883* (2013.01); *A61B 8/463* (2013.01); *A61B 8/5284* (2013.01); *A61B 5/0456* (2013.01); *A61B 8/06* (2013.01); *A61B 8/13* (2013.01)

(58) Field of Classification Search
CPC ........ A61B 8/02; A61B 8/0883; A61B 8/463; A61B 8/5284; A61B 5/0205
USPC .................................................... 600/438, 445
See application file for complete search history.

(56) References Cited

U.S. PATENT DOCUMENTS 8,216,143 B2    7/2012  Gunji
2007/0225611 A1*  9/2007  Kumar et al. ................. 600/523
(Continued)

FOREIGN PATENT DOCUMENTS

JP    H1181852 A    7/1989
JP    04338455 A    11/1992
(Continued)

OTHER PUBLICATIONS

International Search Report, International Application No. PCT/JP2011/069115, filed Aug. 25, 2011, Mailed Nov. 15, 2011, ISA/Japanese Patent Office.
(Continued)

*Primary Examiner* — Baisakhi Roy
(74) *Attorney, Agent, or Firm* — Brundidge & Stanger, P.C.

(57) ABSTRACT

The present invention provides an ultrasonic diagnostic apparatus including a bio-signal analyzing section sequentially acquiring a bio-signal from a bio-signal acquiring section over a plurality of cycles to evaluate stability of a heart function in one cycle between particular signal waveforms of the bio-signal and one cycle between particular signal waveforms adjacent to the one cycle between the particular signal waveforms, selecting the one cycle between the particular signal waveforms and one cycle between the particular signal waveforms adjacent to the one cycle between the particular signal waveforms as a test period for the heart function based on the content of the evaluation, and associating the selected test period with a time phase of the bio-signal.

11 Claims, 12 Drawing Sheets

(51) Int. Cl.
*A61B 8/00* (2006.01)
*A61B 8/06* (2006.01)
*A61B 8/13* (2006.01)
*A61B 5/0456* (2006.01)

(56) References Cited

U.S. PATENT DOCUMENTS

2008/0077012 A1    3/2008  Gunji
2009/0112088 A1*   4/2009  Ohuchi et al. ................ 600/438
2010/0074475 A1*   3/2010  Chouno ........................ 382/107
2010/0106209 A1*   4/2010  Gunderson et al. ............. 607/17

FOREIGN PATENT DOCUMENTS

| | | |
|---|---|---|
| JP | 08-317921 | 12/1996 |
| JP | 11-181852 | 7/1999 |
| JP | 2006-340838 | 12/2006 |
| JP | 2007-020799 | 2/2007 |
| JP | 2007020799 A | 2/2007 |
| JP | 200873282 A | 4/2008 |
| JP | 2009-050683 | 3/2009 |
| JP | 2009-072572 | 4/2009 |
| WO | 2006-068079 | 6/2006 |
| WO | 2012-029616 | 3/2012 |

OTHER PUBLICATIONS

Chinese Office Action, dated Feb. 12, 2015.
Chinese Office Action, dated Jul. 24, 2014.
Japanese Office Action.

* cited by examiner

ULTRASONIC DIAGNOSTIC APPARATUS AND METHOD OF RETRIEVING AND DISPLAYING HEART FUNCTION TEST PERIOD

TECHNICAL FIELD

The present invention relates to an ultrasonic diagnostic apparatus and a method of retrieving and displaying a heart function test period in which a test period in a bio-signal suitable for use in a heart function test is retrieved and then output and displayed on a display screen to improve the efficiency in the heart function test for an object.

BACKGROUND ART

Heart functions are closely correlated not only with electrocardiogram waveforms (electrocardiograms) but also with bio-signals periodically changing due to motions of a heart such as pulses, blood pressures, and heart sounds, so that those bio-signals are used to perform a heart function test. The hear function test involves displaying section images of organs with an ultrasonic diagnostic apparatus over several cycles of the periodically changing bio-signal and computing measurement data representing the hear functions such as the bloodstream state, bloodstream rate, annulus rate, atrium volume, and heart wall motions.

It is presumed that the heart function test should desirably be performed with a plurality of cycles of the bio-signal remaining stable. Thus, ultrasonic measurement data including ultrasonic image data is acquired in association with the changes of the bio-signal and is once stored in a storage section such as a cine memory. Then, for example, a tester retrieves the cycle in which the bio-signal is stable while seeing the bio-signal and the reproduced image of the ultrasonic measurement data, and sets the retrieved cycle to a test period to perform the heart function measurement.

In a case with arrhythmia having unstable pulses, the electrocardiogram waveforms stored in the cine memory are reproduced, and the tester advances frames one by one using an input unit to retrieve the period with stable pulses while seeing the electrocardiogram waveforms.

In Non-Patent document 1, time intervals (R-R time) between two adjacent R waves from one R wave (heart beat) to the next R wave are sequentially measured on the basis of electrocardiogram waveforms, and a tester manually retrieves with an input unit, as a conforming period, the period in which the ratio between two adjacent R-R times is approximately one, and specifies the R-R time immediately after the conforming period as a test period. The hear function measurement is performed in the test period. The measurement is shown to be valid as the measurement value in the case with arrhythmia.

According to the method described in Non-Patent document 1, however, the retrieval of the conforming period requires the tester to watch the displayed image to determine whether or not the ratio between the two adjacent R-R times falls within the allowable range to retrieve the conforming period while he manually reproduces the bio-signal with the input unit. This causes time and effort and a burden on the tester, and in addition, when the tester erroneously retrieves the conforming period, he may retrieve an inappropriate test period as a result.

On the other hand, Patent Document 1 has proposed that the waveforms from a certain R wave to the second earlier R wave are taken on the basis of the history of electrocardiogram waveforms, the difference between the two R-R times included therein is calculated, and when the time difference is equal to or lower than a preset threshold value, that period is evaluated as a conforming period in which pulses are stable.

PRIOR ART REFERENCES

Patent Literature

Patent Literature 1: JP-A-1-181852

Non-Patent Literature

Non-Patent Literature 1: Tomotsugu Tabata, et al., Assessment of LV systolic function atrial fibrillation using an index of preceding cardiac cycles, Am J physiol Heart Circ Physiol 281: H573-H580, 2001

SUMMARY OF THE INVENTION

Problems that the Invention is to Solve

According to the method described in Patent Document 1, however, the difference between the time intervals of the plurality of conforming periods (evaluation value) for which the test period is specified is not output for display, so that the tester has difficulty in comparing the evaluations of the plurality of retrieved test periods and may not determine the reliability of the measurement data provided from the heart function measurement based on the bio-signal in one test period. As a result, the heart function measurement is performed again in the other test periods as a precaution. Thus, Patent Document 1 requires the heart function measurement again and has the unsolved problem in which the efficiency of the heart function test needs to be improved.

It is an object of the present invention to provide an ultrasonic diagnostic apparatus capable of efficiently performing a heart function test based on a bio-signal and a method of retrieving and displaying a heart function test period.

Means for Solving the Problems

To achieve the above object, the present invention includes a bio-signal analyzing section sequentially acquiring a bio-signal from a bio-signal acquiring section over a plurality of cycles to evaluate stability of a heart function in one cycle between particular signal waveforms of the bio-signal and one cycle between particular signal waveforms adjacent to the one cycle between the particular signal waveforms, selecting the one cycle between the particular signal waveforms and one cycle between the particular signal waveforms adjacent to the one cycle between the particular signal waveforms as a test period for the heart function based on the content of the evaluation, and associating the selected test period with a time phase of the bio-signal.

Advantage of the Invention

According to the present invention, the heart function test based on the bio-signal can be performed efficiently.

BEST MODE FOR CARRYING OUT THE INVENTION

Figure 1:
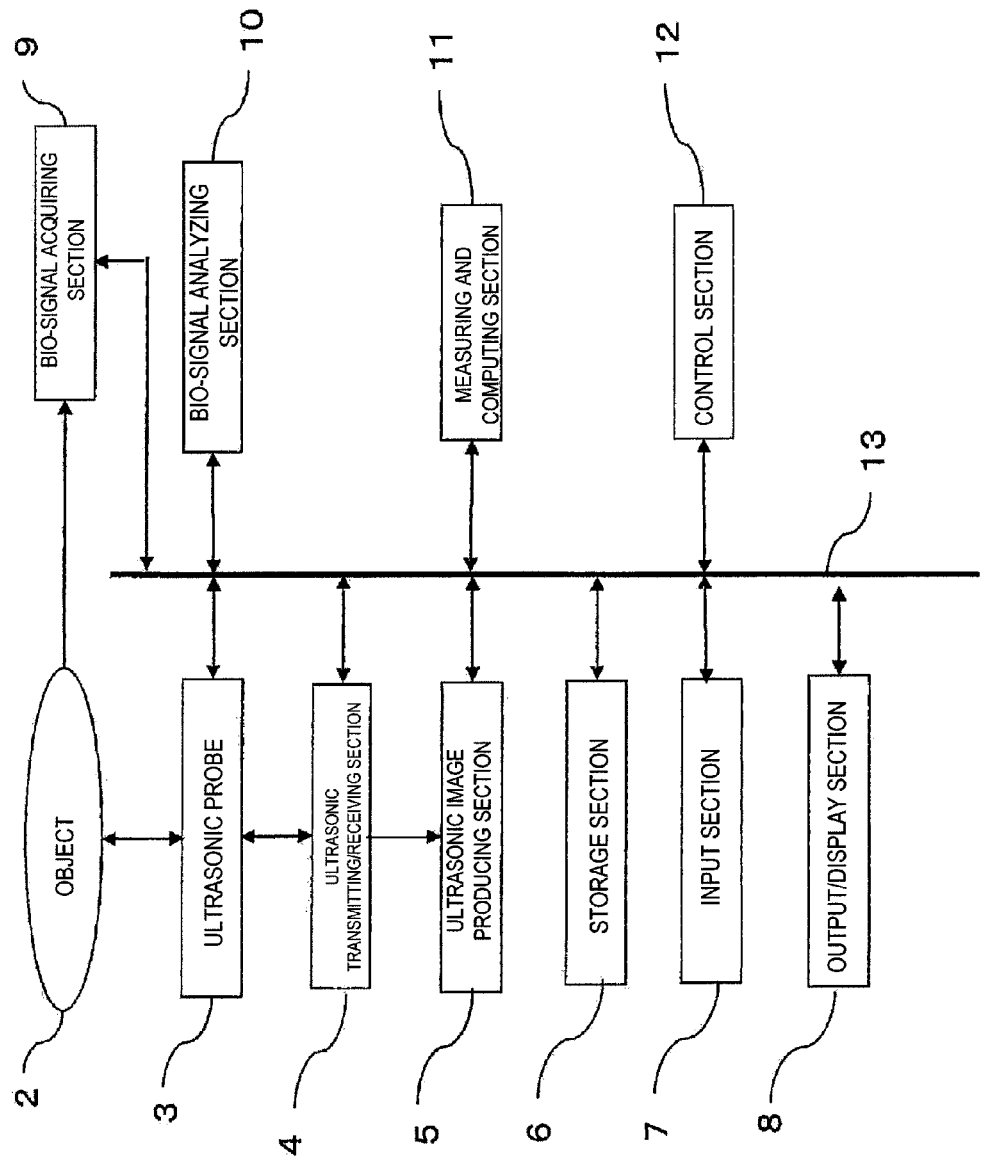
FIG. 1 A block schematic diagram of an ultrasonic diagnostic apparatus according to an embodiment for performing a method of retrieving and displaying a heart function test period in the present invention.

Referring to FIG. 1 showing a block schematic diagram, description is made of an ultrasonic diagnostic apparatus according to an embodiment of the present invention implementing a method of retrieving and displaying a heart function test period. As shown, an ultrasonic diagnostic apparatus 1 is formed to include an ultrasonic probe 3, an ultrasonic transmitting/receiving section 4, an ultrasonic image producing section 5, a storage section 6, an input section 7, an output/display section 8, a bio-signal acquiring section 9, a bio-signal analyzing section 10, a measuring and computing section 11, a control section 12, and a system bus 13.

The ultrasonic probe 3 is formed to include a plurality of oscillators for transmitting and receiving ultrasonic to and from an object 2 which is an organ of interest. The ultrasonic probe 3 may be provided by using a scan method of a linear type, a convex type, and a sector type.

The ultrasonic transmitting/receiving section 4 receives information about the power and the timing of an ultrasonic signal to be transmitted and received from the control section 12 and controls the ultrasonic probe 3 such that a predetermined reflection echo signal is acquired. The ultrasonic transmitting/receiving section 4 processes and outputs the reflection echo signal received by the ultrasonic probe 3 to the ultrasonic image producing section 5 and the measuring and computing section 11.

The ultrasonic image producing section 5 passes the reflection echo signal input from the ultrasonic transmitting/receiving section 4 through a phasing circuit and an amplifier circuit to process the signal in accordance with imaging settings provided by the control section 12. The ultrasonic image producing section 5 produces ultrasonic images based on the shaped ultrasonic signal such as a section image of an organ of the object 2, a bloodstream image and an bloodstream rate image based on the Doppler measurement, and an organ Doppler image, for example.

The storage section 6 stores ultrasonic measurement data including the ultrasonic image produced in the ultrasonic image producing section 5, measurement data computed in the measuring and computing section 11, and bio-signal data acquired in the bio-signal acquiring section 9. The storage section 6 also stores a program for realizing the functions of the respective sections constituting the ultrasonic diagnostic apparatus 1. For example, the storage section 6 stores a computation algorithm used in executing the signal analyzing section 10 and the measurement computing section 11.

The input section 7 is an interface for a tester to perform various types of operations in the ultrasonic diagnostic apparatus 1 and includes an input device such as a keyboard, trackball, switch, and dial. For example, the input section 7 is used to perform measurement settings of an organ on an ultrasonic image displayed on a display screen of the output/display section 8 and to move the current time phase of a reproduced image and a test period. The output/display section 8 displays the bio-signal, the ultrasonic image, and the measurement data on the screen or outputs the measurement data in a measurement report.

The bio-signal acquiring section 9 acquires and converts the bio-signal of the object 2 into bio-signal data and stores the data in the storage section 6. The bio-signal acquiring section 9 directly inputs the acquired bio-signal to the bio-signal analyzing section 10 or acquires and inputs the bio-signal from the storage section 6 to the bio-signal analyzing section 10. Specifically, when the bio-signal analyzing section 10 is operated in real time, the bio-signal data is directly input from the bio-signal acquiring section 9 to the bio-signal analyzing section 10. Although an electrocardiogram is a typical example of the bio-signal, the present invention is not limited thereto, and a heart sound diagram or a pulse signal can be used as long as the time intervals between heart beats can be retrieved in the bio-signal.

The bio-signal analyzing section 10 has the function of sequentially acquiring the bio-signal over a plurality of cycles from the bio-signal acquiring section 9, evaluating the stability of heart functions in one cycle between particular signal waveforms of the bio-signal and one cycle between particular signal waveforms adjacent to the one cycle between the particular signal waveforms, selecting the one cycle between the particular signal waveforms and one cycle between the particular signal waveforms adjacent to the one cycle between the particular signal waveforms as a test period of the heart functions based on the evaluations, and associating the selected test period with the time phase of the bio-signal.

In other words, the bio-signal analyzing section 10 retrieves the heart beats in a preset number of successive periods (for example, two) based on the bio-signal data input from the bio-signal acquiring section 9 to compare whether or not the retrieved successive periods have equal heart beat data. The comparison is performed with the computation algorithm stored in the storage section 6. The details are described later.

The measuring and computing section 11 determines through computation the measurement data representing the bloodstream rate, atrium volume, annulus motions, and heart wall motions based on the Doppler measurement and the ultrasonic measurement data of the organ Doppler relating to the heart functions. For example, the measuring and computing section 11 computes the measurement data such as the bloodstream rate in a region of interest (ROI) set with the input section 7 by using the computation algorithm stored in the storage section 6. The measurement values resulting from the computation are stored in the storage section 6 and read out as required. The control section 12 is formed to include a CPU and the like and controls the overall ultrasonic diagnostic apparatus 1. In the present embodiment, the control section 12 particularly controls the synchronization of a series of operations performed in the bio-signal acquiring section 9, the bio-signal analyzing section 10, the measuring and computing section 11, and the output/display section 8. The system bus 13 is a bus on which the data is passed between the respective processing units.

The method of retrieving and displaying the heart function test section characteristics of the present invention will hereinafter be described in individual embodiments. Although the following embodiments are described in conjunction with the use of an electrocardiogram signal as the bio-signal, it goes without saying that the present invention is not limited to the use of the electrocardiogram signal.

Embodiment 1

Figure 2:
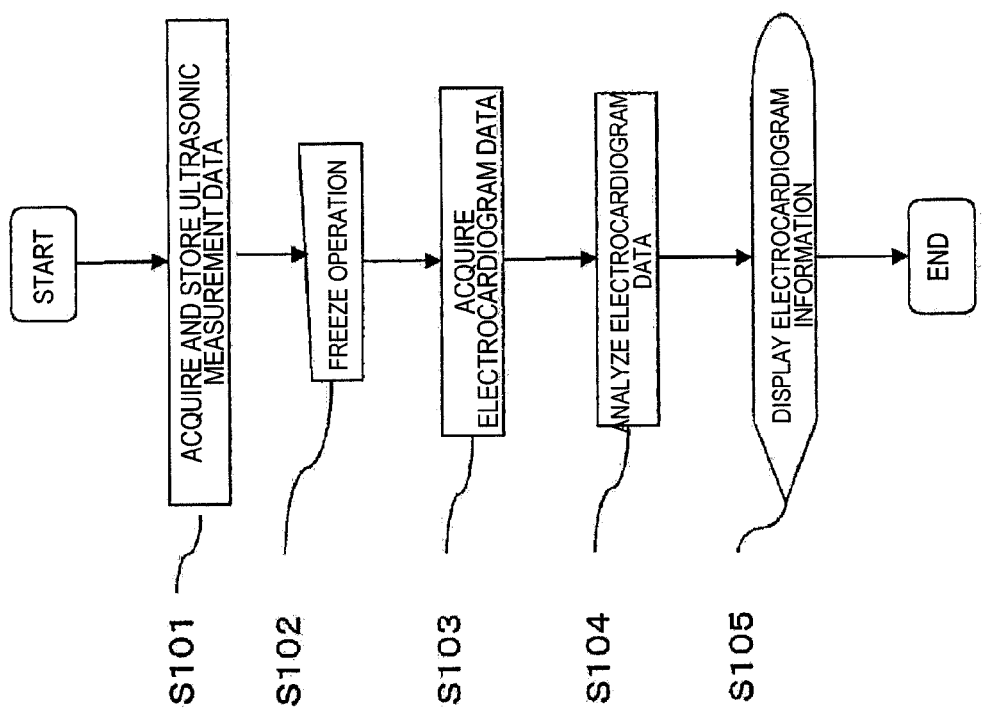
FIG. 2 A flow chart of Embodiment 1 of the method of retrieving and displaying the heart function test period in the present invention.

Embodiment 1 is an example in which electrocardiogram data to be analyzed is previously accumulated in the storage section 6 before analysis. This is an example of so-called off-line processing, and FIG. 2 shows a flow chart of the processing. As shown in FIG. 2, electrocardiogram data is acquired by the bio-signal acquiring section 9, the ultrasonic probe 3 is brought into contact with the object 2 to transmit and receive ultrasonic under predetermined imaging conditions to perform ultrasonic measurement, and the ultrasonic measurement data including the acquired ultrasonic image data and Doppler measurement data is stored in the storage section 6 (S101). At this point, for example, moving images including an electrocardiogram waveform diagram and an ultrasonic image are displayed on the display screen of the output/display section 8.

Next, when the tester performs freeze operation with the input section 7, the output of the images to the display screen by the output/display section 8 is stopped (S102). At this point, the storage section 6 has the accumulated ultrasonic measurement data and electrocardiogram data acquired at S102. Then, the bio-signal acquiring section 9 is activated to acquire the electrocardiogram data of a range to be analyzed from the electrocardiogram data stored in the storage section 6 (S103).

The bio-signal producing section 8 may be activated after the freeze or may be executed by pressing an electrocardiogram data analyzing button provided for the input section 7.

Upon start of the operation, the bio-signal acquiring section 9 extracts the electrocardiogram data of the required time range from the electrocardiogram data accumulated in the storage section 6. The range to be analyzed may be all the accumulated electrocardiogram data or only the period displayed as waveforms on the screen of the output/display section 8, for example. The range of the electrocardiogram data to be analyzed can be narrowed to reduce the analyzing time to smooth the operation of the apparatus, thereby providing the effect of improving the test efficiency.

Figure 3:
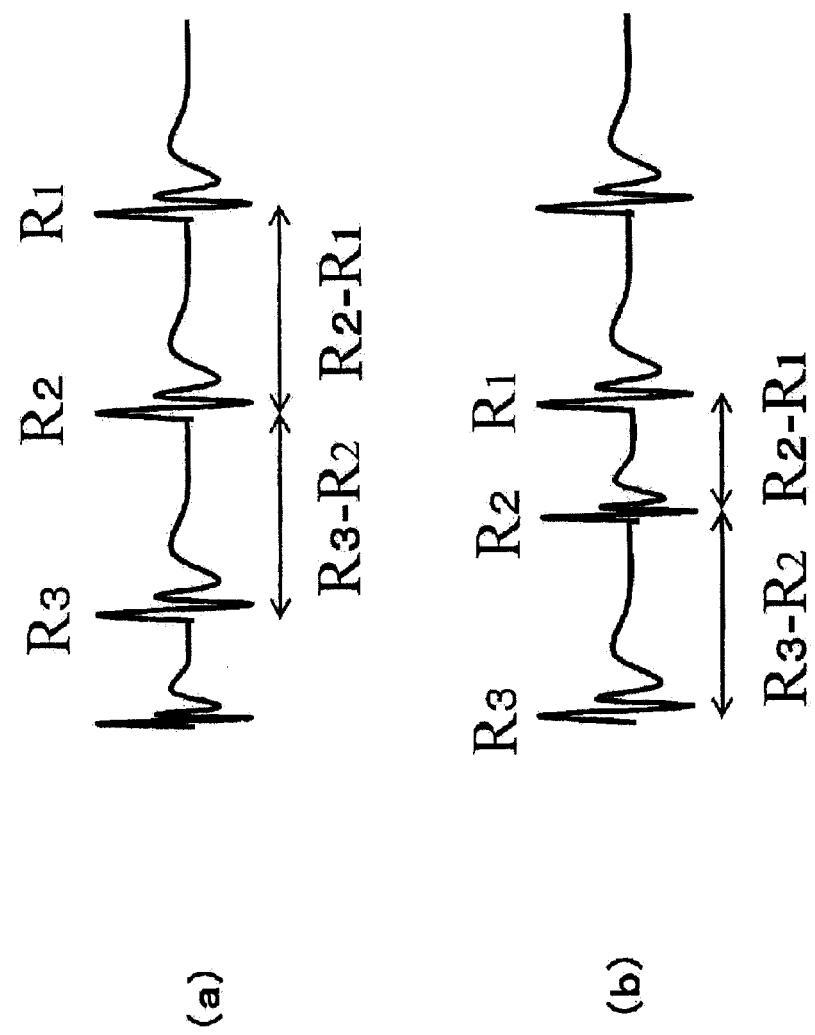
FIG. 3 Diagrams showing examples of electrocardiogram waveforms for describing the operation of Embodiment 1.

The electrocardiogram data read out from the storage section 6 by the bio-signal acquiring section 9 is input to the bio-signal analyzing section 10 to perform the analysis of the electrocardiogram data (S104). The analysis of the electrocardiogram data in the bio-signal analyzing section 10 is described with reference to FIG. 3. As shown in FIG. 3(a) and FIG. 3(b), R waves in the electrocardiogram waveform are set to particular signal waveforms. Each time the R wave is input, the bio-signal analyzing section 10 retrieves the time interval between that R wave and the previously input R wave. For example, as shown in FIG. 3(a), assuming that the electrocardiogram waveform is input in the order of R3, R2, then R1, the bio-signal analyzing section 10 determines a time interval R3-R2 between R3 and R2 corresponding to one cycle of the electrocardiogram waveform and a time interval R2-R1 between R2 and R1 corresponding to the adjacent one cycle of the electrocardiogram waveform. When a comparison between the two adjacent time intervals shows that they are approximately equal, the bio-signal analyzing section 10 assumes that the pulses are regular and stable, and retrieves those R-R periods as a conforming period. On the other hand, in FIG. 3(b), an interval R2-R1 is shorter than an interval R3-R2, so that the bio-signal analyzing section 10 assumes that the pulses are irregular and unstable, and sets those periods as non-conforming periods.

The following three methods are contemplated as the specific methods of using the two adjacent time intervals R3-R2 and R2-R1 to evaluate the stability of the heart functions to select or retrieve the conforming period.

(1) As the ratio between the two adjacent time intervals R3-R2 and R2-R1 is closer to one, the stability evaluation value is higher.

FIG. 3(a) shows the example in which (R2-R1)/(R3-R2) is approximately one and the evaluation value of the stability is high. FIG. 3(b) shows the example in which (R2-R1)/(R3-R2)<<1 and the evaluation value of the stability is low. Thus, in FIG. 3(a), the R3-R2 period and the R2-R1 period are retrieved as the conforming periods. The period immediately after the conforming period R1 is specified as a test period suitable for the heart function measurement. In this case, the ratio between the time intervals of the two R-R periods evaluated as the conforming periods is compared with a preset threshold value. The threshold value can be set as a range having the lower limit and upper limit such that the lower limit is 0.95 and the upper limit is 1.05, for example. The threshold value can be set by the tester using the input section 7, or a standard value can be preset for the apparatus.

(2) As the absolute value of the difference between the two adjacent time intervals R3-R2 and R2-R1 is closer to zero, the stability evaluation value is higher.

FIG. 3(a) shows the example in which |(R3-R2)−(R2-R1)| is approximately zero and the evaluation proves high stability. FIG. 3(b) shows the example in which |(R3-R2)−(R2-R1)|>>0 and the evaluation proves low stability. While the threshold value for the evaluation is also set in this case, the threshold value is set to 50 ms or less, for example, since it represents the difference in time intervals.

(3) As the matching between the waveforms of the two adjacent R-R periods is higher, the evaluation value of the stability is higher.

In the example shown in FIG. 3, the matching between the R3-R2 waveform and the R2-R1 waveform is used as an evaluation criterion. The matching between the waveforms is evaluated not only with the correlation coefficient of both waveforms and but also by previously storing a normal waveform in the storage section 6 and performing pattern matching between the normal waveform and the R-R waveform. When the matching falls within a preset range of threshold values, that R-R period is retrieved as the conforming period.

Since the above evaluation methods (1) and (2) involve simple computation, they have the advantages such as short calculation times, smooth operation of the apparatus, and excellent operability of the apparatus. On the other hand, the evaluation method (3) can evaluate the stability of the electrocardiogram waveform more precisely than in the evaluations methods (1) and (2), but the method (3) requires a long time for the computation to result in less smooth operation of the apparatus.

Figure 4:
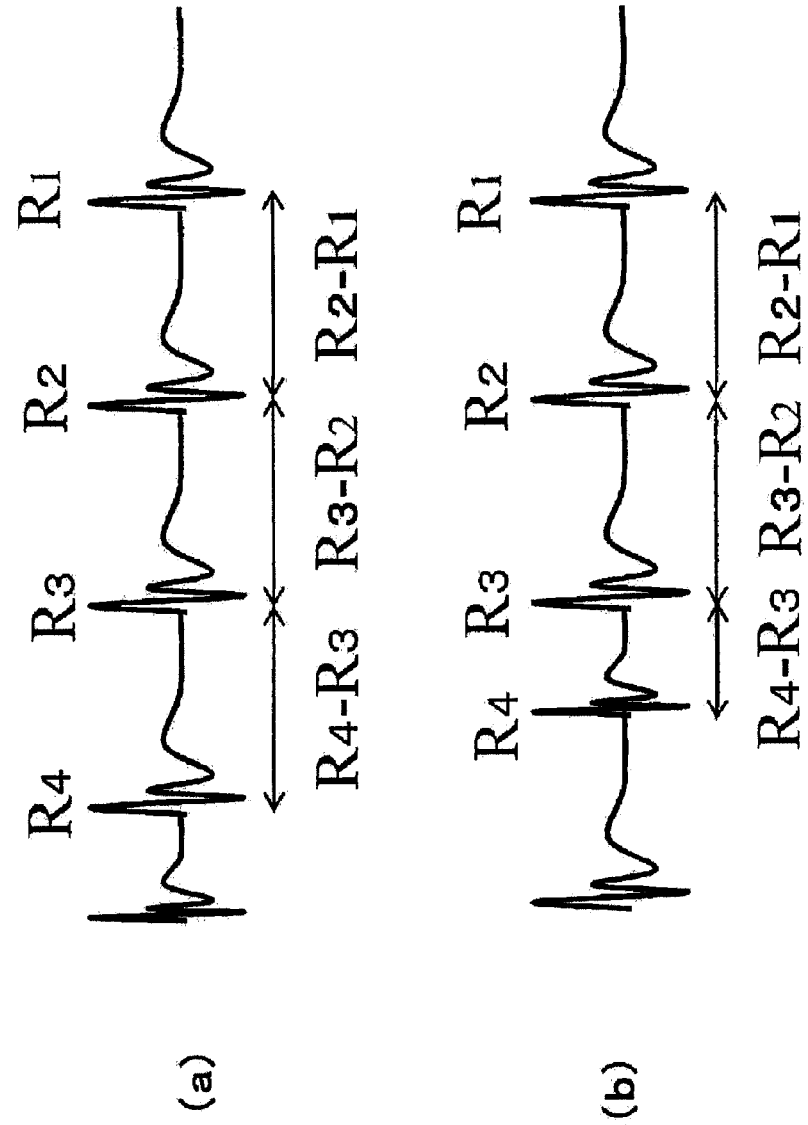
FIG. 4 Diagrams showing other examples of electrocardiogram waveforms for describing the operation of Embodiment 1.

The above evaluation methods (1), (2), and (3) have been described with the example in which the stability is evaluated on the basis of the difference between the two adjacent R-R periods and the like to retrieve the conforming period. It goes without saying that the present invention is not limited thereto and that the stability can be evaluated on the basis of three or more adjacent R-R periods to retrieve the conforming period. For example, FIG. 4(*a*) and FIG. 4(*b*) show examples in which three successive time intervals R4-R3, R3-R2, and R2-R1 are used to evaluate the stability of the heart functions. In the example shown in FIG. 4(*a*), since the ratio or the difference between the three successive time intervals satisfies an evaluation threshold value or satisfies an evaluation threshold value for the matching between the waveforms of the three successive time intervals, the electrocardiogram cycle immediately after the last conforming period R1 is specified as the test period. On the other hand, in the example shown in FIG. 4(*b*), since the time interval or the waveform between R4 and R3 is significantly different from those of the other two R-R intervals, those periods are not conforming periods. Thus, the electrocardiogram cycle immediately after the R2-R1 interval cannot beset to the test period. Similar evaluation can be performed for four or more successive intervals. The number of the successive intervals can be set to a value by the tester using the input section 7 or a standard value can be preset for the apparatus.

According to the method of evaluating the test period suitable for the heart function measurement described above, the stable heart beats can be set selectively to be shorter or longer depending on the severity of the arrhythmia of the object to improve the usability of the apparatus.

The method of evaluating the conforming period described above is applied to the entire range of the electrocardiogram data acquired at step S103 in FIG. 2. For each R-R period for which the computation is performed, the relevant information is stored in the storage section 6 such as the evaluation value of the ratio or the difference or the matching, the R-R time interval, and the serial number given to the specified test period.

Figure 5:
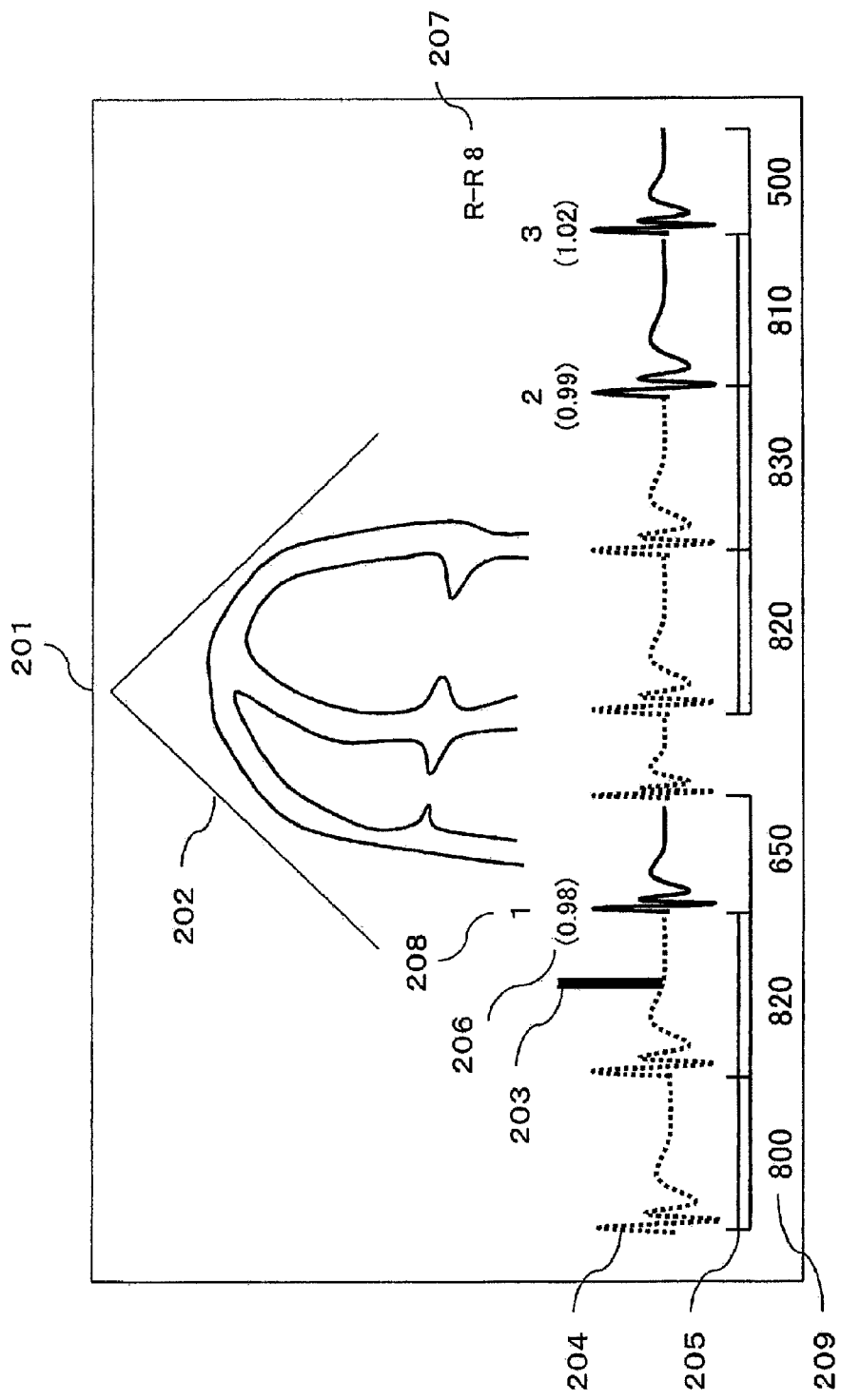
FIG. 5 An exemplary display screen showing the result of retrieval of the heart function test period retrieved according to Embodiment 1.

Next, at step S105 in FIG. 2, the output/display section 8 functions to display the electrocardiogram information of the test period and the preceding R-R periods involved in the evaluation as shown in FIG. 5. FIG. 5 shows an example of a display screen 201 of the output/display section 8 immediately after the completion of step S104 at which the electrocardiogram data is analyzed. As shown, the analysis of the electrocardiogram data is performed in the range of an electrocardiogram waveform 204 displayed on the screen. FIG. 5 shows the example in which the number of successive R-R periods used for retrieving the conforming periods is set to two. An ultrasonic image 202 which is the section image of the heart is displayed on the display screen 201. The ultrasonic image 202 is the section image of the heart at the position of a time phase bar 203 on the time axis displayed on the electrocardiogram waveform 204. Thus, the time phase bar 203 represents the time phase of the currently reproduced ultrasonic image 202 on the electrocardiogram waveform. Instead of or together with the ultrasonic image 202, the measurement value calculated in the measuring and computing section 11 or the Doppler waveform may be displayed.

Below the electrocardiogram waveform 204, a range 205 of the time axis including two R-R periods evaluated as the conforming periods and the test period is displayed, and the time (ms) of each R-R period is displayed. The evaluation value of the stability is displayed at the R wave time phase at the beginning of the test period. For example, in the left half of the electrocardiogram waveform 204, the time intervals of the two R-R periods serving as the conforming periods are 800 and 820, respectively. Thus, the ratio (evaluation value) thereof is approximately 0.98. The evaluation value is displayed as an evaluation value 206 above the R wave time phase at the beginning of the test period subsequent to the conforming periods. In an example shown in the right half of the electrocardiogram waveform 204, the evaluation proves high stability of two adjacent R-R periods in the three successive periods. In this case, when the stability is evaluated with the set number equal to two, the two test periods are specified and the two evaluation values are calculated in the conforming periods of the first two periods and the conforming periods of the second two periods. Thus, FIG. 5 shows the evaluation values 206 of 0.99 and 1.02 at the two positions of the R waves. In addition, the number of all the R-R periods (R-R8) 207 retrieved within the range of the electrocardiogram data acquired at step S103 is displayed. Serial numbers 208 are displayed at the positions of the R wave time phases at the beginnings of the test periods.

The test periods are highlighted by solid lines and the other R-R periods are displayed by broken lines to allow visual recognition. The highlighting of the test periods may be performed by changing the color of or blinking the electrocardiogram waveform in the test periods. For example, although the range 205 of the time axis of the conforming periods is shown by double lines in FIG. 5, the double lines may be shown in light color and the range 205 of the test period may be highlighted in dark color. Alternatively, the range 205 of the test period may be blinked. When the time phase bar 203 representing the time phase of the reproduced ultrasonic image 202 is present outside the test period as in the example of FIG. 5, the ultrasonic image 202 in that time phase is not appropriate for the analysis of the hear functions. Thus, the display may be more apparent to the tester by coloring or blinking the frame 202 of the image, shading or darkening the ultrasonic image 202. When the time phase bar 203 is present outside the conforming periods and the test periods, the display may be more apparent to the tester similarly by coloring or blinking the frame 202 of the image.

Figure 6:
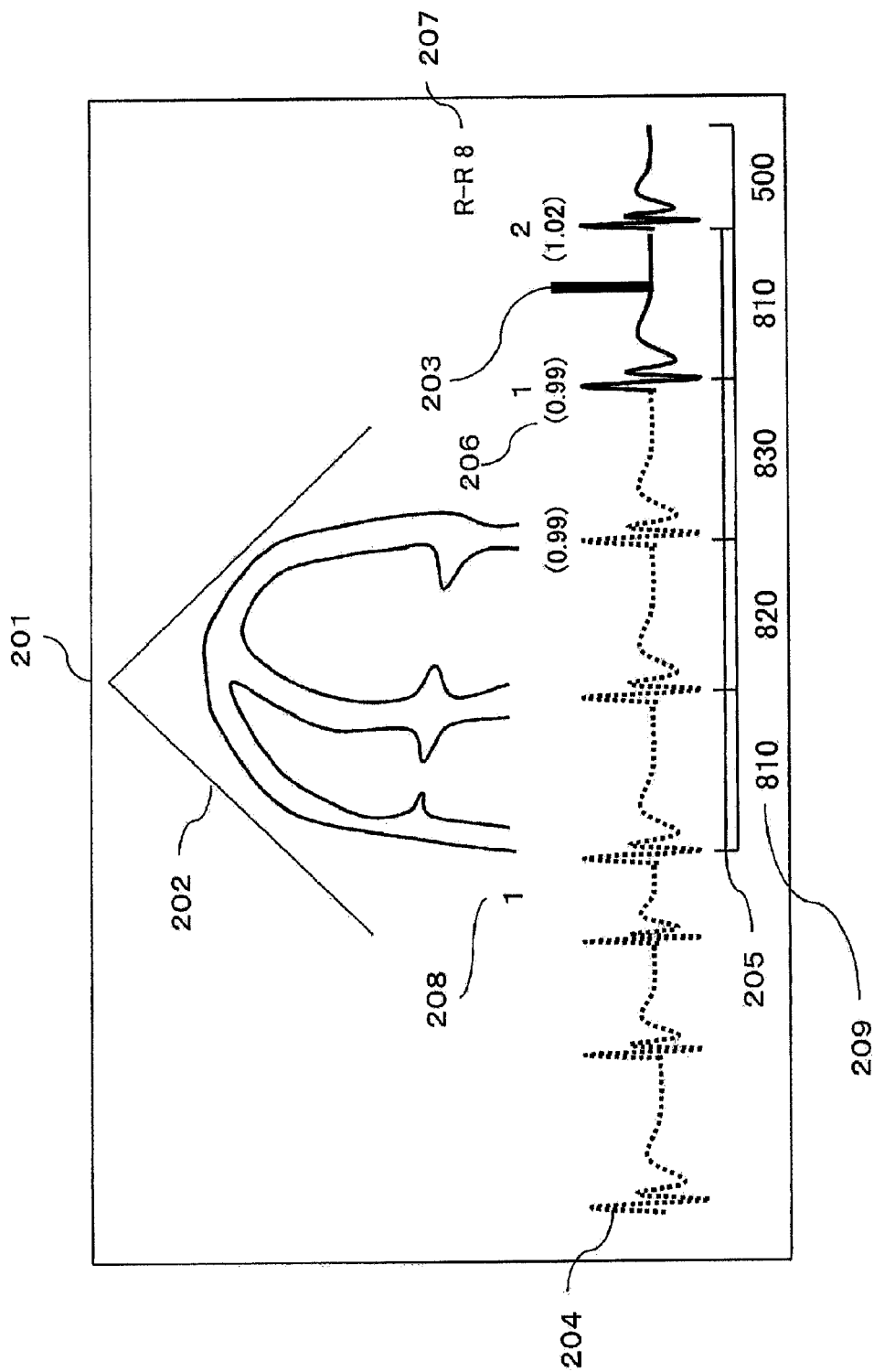
FIG. 6 Another exemplary display screen showing the result of retrieval of the heart function test period retrieved according to Embodiment 1.
Figure 7:
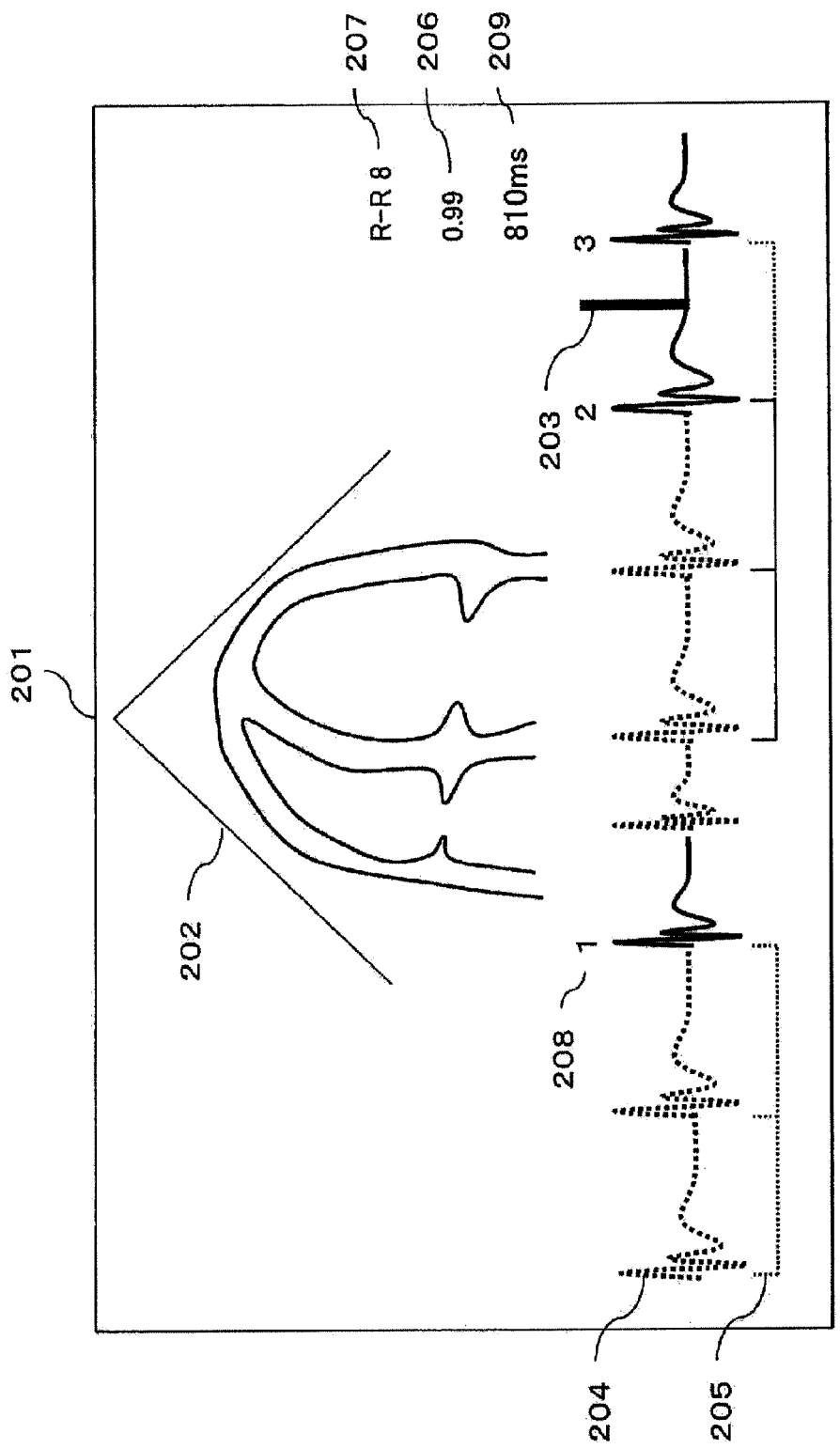
FIG. 7 Yet another exemplary display screen showing the result of retrieval of the heart function test period retrieved according to Embodiment 1.

Next, other display examples of the display screen according to Embodiment 1 are shown in FIG. 6 and FIG. 7. FIG. 6 shows a display screen 201 immediately after the completion of the electrocardiogram data analysis at S104. The example in FIG. 6 shows the entire range of the electrocardiogram waveform 204 in which the electrocardiogram data to be analyzed is displayed on the screen, and illustrates the case in which the set number of the successive conforming periods for evaluating the stability is set to three. FIG. 6 shows the display similar to that in FIG. 5, and the time intervals between R-R periods are measured and displayed as 810, 820, and 830 (ms) in order. The ratios between the time intervals of the two adjacent R-R periods are 0.99 and 0.99 in order. Thus, the evaluation value 0.99 is displayed as an evaluation value 206 above the last R wave of the two adjacent R-R waves. In the example of FIG. 6, the three successive R-R periods satisfying the stability evaluation condition continue, so that the two test periods are retrieved and the evaluation value 1.02 is displayed as the evaluation value 206.

In the example of the display shown in FIG. 7, the information displayed in addition to the electrocardiogram waveform is minimized to improve visual recognition. Since the examples of the display screen shown in FIG. 5 and FIG. 6 display much information around the electrocardiogram waveform, some testers have difficulty in finding important information. In the present example, when the time phase bar 203 is located in any of the two R-R periods for which the stability is evaluated, the range 205 of those R-R periods is highlighted. The evaluation value 206 and the R-R time 209 are displayed in a different region (right region in the shown example) not around the electrocardiogram waveform. When the time phase bar 203 is moved to any of the two R-R periods for which the stability is evaluated, for example by using a track ball of the input section 7, the evaluation value 206 and the R-R time 209 are overwritten in the heart beat to which the movement is made. In addition, the display of the range 205 is also moved and highlighted.

According to Embodiment 1 described above, the limited electrocardiogram data to be analyzed is acquired, and the calculation is performed on that data for retrieving the test period, so that the amount of the calculation can be reduced to reduce the load on the apparatus. This can smooth the operation of the apparatus to improve the test efficiency.

Since the retrieved test periods are highlighted, the tester can have access easily.

When the possibly suitable test periods are ranked on the basis of the evaluation values and are displayed in different colors in accordance with the ranks, the usability is further improved.

Since the tester can select and set the evaluation conditions such as the ratio and the difference between the adjacent R-R periods and the matching between the waveform patterns in the electrocardiogram data analysis, the conforming period for retrieving the test period can be appropriately retrieved. As a result, the conforming period and the test period appropriate for the symptoms can be retrieved, so that the excellent usability is achieved.

In addition, since the number of the adjacent successive R-R periods for which the stability is evaluated can be changed, the retrieval of the conforming period can be performed depending on the severity of arrhythmia, thereby improving the usability of the apparatus.

When the display screen is switched between the display of various information of the electrocardiogram on the electrocardiogram waveform and the display of the information in a different region on the screen rather than the electrocardiogram waveform, detailed analysis and simple analysis can be performed individually to allow the selection fit for the use of the tester.

Embodiment 2

Figure 8:
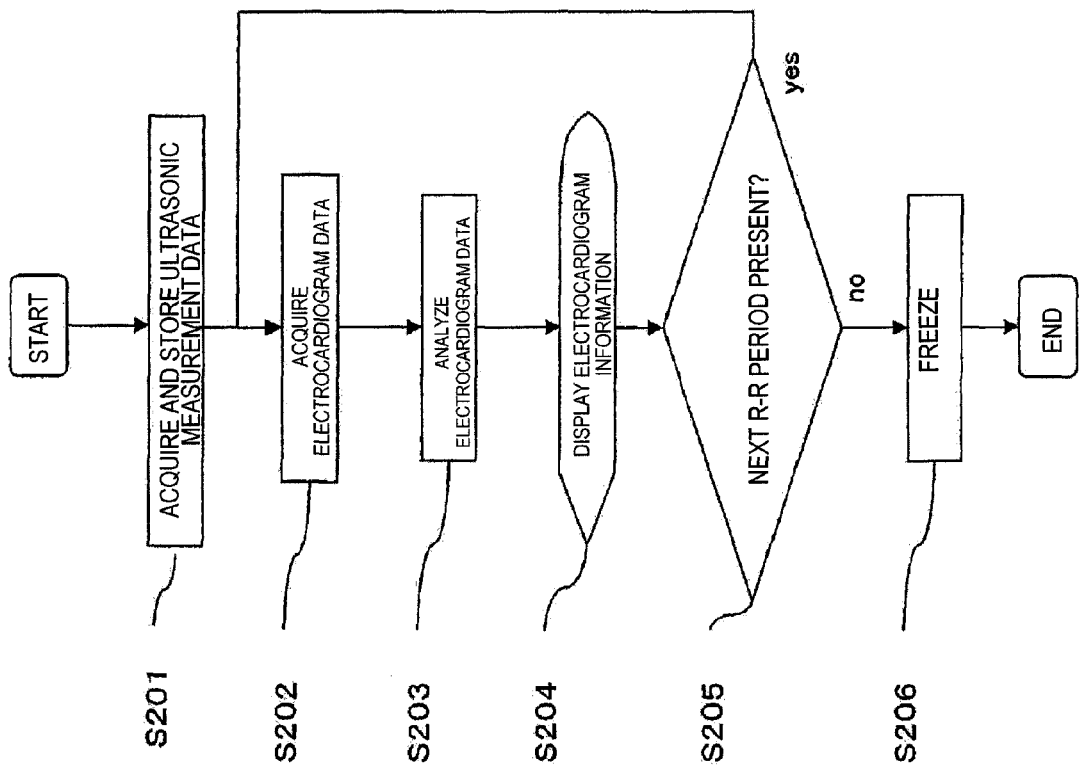
FIG. 8 A flow chart of Embodiment 2 of the method of retrieving and displaying the heart function test period in the present invention.

Embodiment 2 is an example in which electrocardiogram data to be analyzed is successively stored in the storage section 6 and is analyzed at the same time. This is the example of so-called real-time processing, and FIG. 8 shows a flow chart of the processing. In the present embodiment, similarly to Embodiment 1, at step S201, the electrocardiogram data is acquired by the bio-signal acquiring section 9, and the tester brings the ultrasonic probe 3 into contact with the object 2, transmits ultrasonic under predetermined imaging conditions to perform the ultrasonic test, and stores the acquired electrocardiogram waveform diagram, ultrasonic image data, Doppler measurement data and the like in the storage section 6, and the moving image of the ultrasonic image is displayed on the display screen of the output/display section 8. In this state, the function of the bio-signal analyzing section 10 is valid through the operation of the input section 7 by the tester. Description is made assuming the set number of adjacent successive R-R periods serving as the condition for retrieving the conforming periods is two.

First, the bio-signal acquiring section 9 acquires the electrocardiogram data newly stored in the storage section 6 and inputs the acquired data to the bio-signal analyzing section 10 (S202). The bio-signal analyzing section 10 analyzes the sequentially input electrocardiogram data (S203). Specifically, the bio-signal analyzing section 10 performs an evaluation to determine whether or not the ratio or the difference between the time interval of the latest two R-R periods stored in the storage section 6 or the matching between the waveform patterns in those R-R periods satisfies a threshold value. When the threshold value is satisfied as a result of the evaluation, those R-R periods are set to the conforming periods to perform retrieval. Similarly to Embodiment 1, various types of information relating to the electrocardiogram waveform are displayed on the display screen 201 as shown in FIG. 5 (S204). When the next R wave is retrieved and the new R-R period is stored in the storage section 6, the control returns to step S202 to repeat the same processing (S205). Then, when a freeze instruction is input through the input section 7, the storage of the new electrocardiogram data in the storage section 6 is stopped to end the processing of the bio-signal analyzing section 10 (S206).

Figure 9:
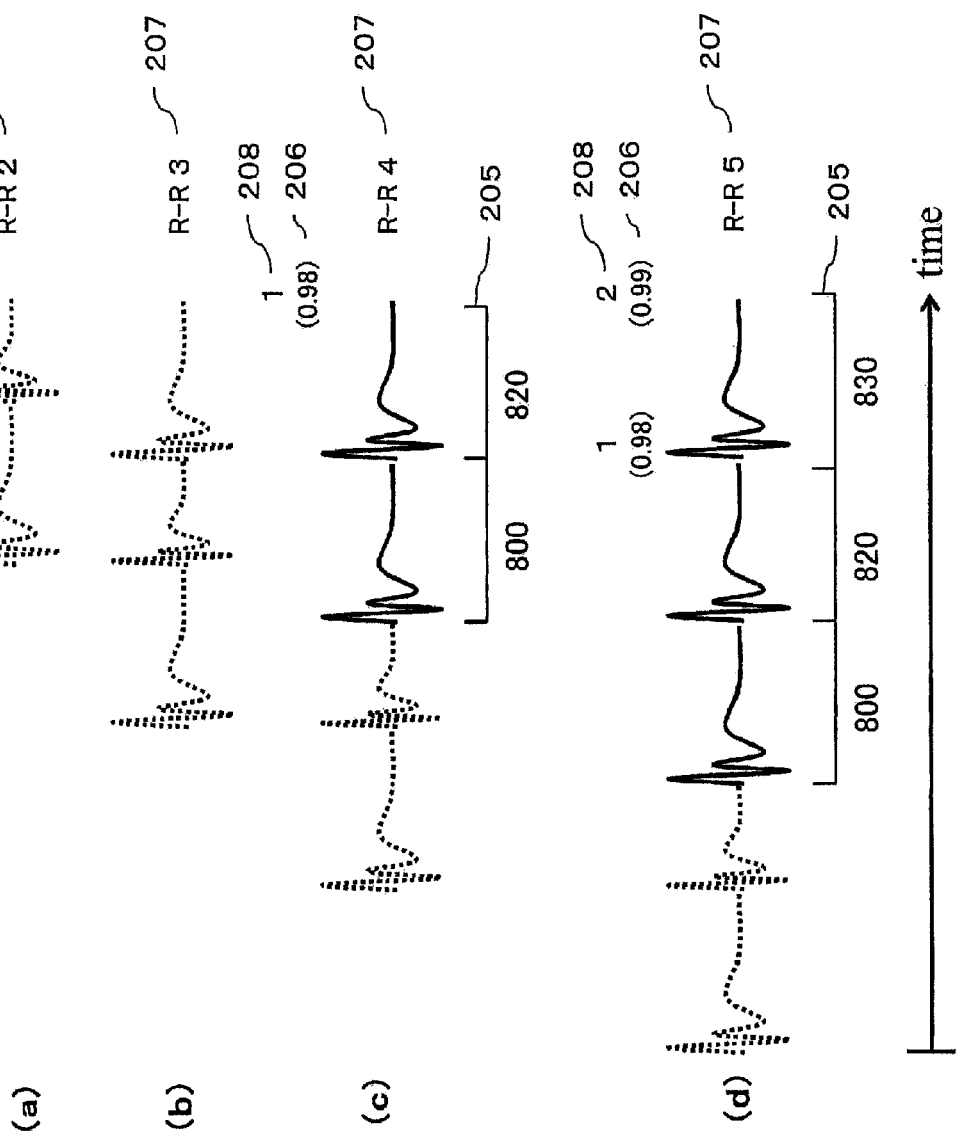
FIG. 9 Diagrams for describing changes in the operation of Embodiment 2.

FIG. 9 illustrates the operation in Embodiment 2 represented on a time axis and shows changes over time of the electrocardiogram waveform and relating information displayed on the screen. FIG. 9(a) shows the point in time at which two R-R periods have been stored in the storage section 6 after the start of the acquisition of the electrocardiogram data. At this point, the electrocardiogram data is acquired from the storage section 6 by the bio-signal acquiring section 9 and is input to the bio-signal analyzing section 10. The bio-signal analyzing section 10 analyzes the input two R-R periods and performs an evaluation to determine that the two R-R periods do not have the same electrocardiogram waveform. Thus, the electrocardiogram waveform displayed on the display screen is not highlighted or the electrocardiogram information is not displayed. The number of R-R periods (R-R2) 207 is displayed.

FIG. 9(b) shows the point in time at which the third R-R period has been stored in the storage section 6 after the start of the acquisition of the electrocardiogram data. At this point, the new third R-R period is input to the bio-signal analyzing section 10 through the bio-signal acquiring section 9. The bio-signal analyzing section 10 analyzes the newest R-R period data and the preceding R-R period data and performs an evaluation to determine whether or not the second and third R-R periods are conforming periods. In the example of FIG. 9(b), the evaluation proves that the second and third R-R periods are not conforming periods. Thus, the electrocardiogram waveform is not highlighted or the electrocardiogram information is not displayed.

FIG. 9(c) shows the point in time at which the fourth R-R period has been stored in the storage section 6 after the start of the acquisition of the electrocardiogram data. At this point, the new fourth R-R period is input to the bio-signal analyzing section 10 through the bio-signal acquiring section 9. The bio-signal analyzing section 10 analyzes the newest R-R period data and the preceding R-R period data and performs an evaluation to determine whether or not the third and fourth R-R periods are conforming periods. In this example, the newest R-R period and the preceding R-R period are the same and two successive periods, so that those R-R periods are evaluated as the conforming periods. Thus, the time intervals and ranges 205 of the R-R periods, the evaluation value 206, and the serial number 208 are displayed on the display image. At the same time, the electrocardiogram waveform is highlighted.

FIG. 9(d) shows the point in time at which the fifth R-R period has been stored in the storage section 6 after the start of the acquisition of the electrocardiogram data. At this point, the new fifth R-R period is input to the bio-signal analyzing section 10 through the bio-signal acquiring section 9. The bio-signal analyzing section 10 analyzes the newest R-R period data and the preceding R-R period data and performs an evaluation to determine whether or not the fourth and fifth R-R periods are conforming periods. In this example, the newest R-R period and the preceding R-R period are the same and two successive periods, so that those R-R periods are evaluated as the conforming periods. Thus, the time intervals and ranges 205 of the R-R periods, the evaluation values 206, and the serial numbers 208 are displayed on the display image. At the same time, the electrocardiogram waveform is highlighted.

When freeze is performed at step S206, the acquisition of various types of information in the ultrasonic diagnostic apparatus can be stopped, and after the stop, display similar to that in Embodiment 1 can be performed.

According to Embodiment 2, since the R-R period is stored in the storage section 6 with each heart beat, the R-R periods are sequentially processed and the results are displayed on the display screen of the output/display section 8 in real time.

Since the information about the electrocardiogram waveform including the results of the evaluation of the respective R-R periods is stored in the storage section 6, the tester can access the previous data, for example through the operation of the track ball of the input section 7, and the processing similar to that in Embodiment 1 can be performed.

As described above, according to the present embodiment, the R-R period data taken in real time by the storage section 6 can be acquired to perform the evaluation to determine immediately whether or not the set number of adjacent R-R periods are conforming periods. In other words, while the ultrasonic image is displayed, the conforming period suitable for the heart function measurement can be retrieved in real time to specify the test period. The freeze is performed at the time when the test period is specified, which allows the tester to easily access the heart beat cycle appropriate for the heart function measurement to perform the measurement processing. This can result in the improved efficiency of the test. Since the analyzed electrocardiogram data is stored in the storage section 6, the tester can also access the heart beat cycle of the past.

Embodiment 3

Embodiment 3 is characterized in that a series of data for electrocardiographically analyzing functions stored in the storage section 6 is reproduced by jumping to a specified test period. In other words, Embodiment 3 is characterized by having the function of capable of access only to the test period specified in Embodiments 1 and 2 and stored in the storage section 6 and relates to a method of use after the completion of the processing in Embodiments 1 and 2.

In general, when display of the ultrasonic image in a desired time phase on the screen is desired, the tester manipulates, for example the track ball of the input section 7, to display the images stored in the storage section 6 one by one for searching while checking the images. Embodiment 3 is characterized in that, since the time phase of the data for electrocardiographically analyzing the functions useful in the heart function measurement is the time phase in the test period, the direct access to the test period is allowed without burdensome searching. In Embodiments 1 and 2, the test periods are given the serial numbers and stored in the storage section 6. In contrast, in the present embodiment, the direct jumping of the time phase to the test period enables the efficient access to the desired test period.

Figure 10:
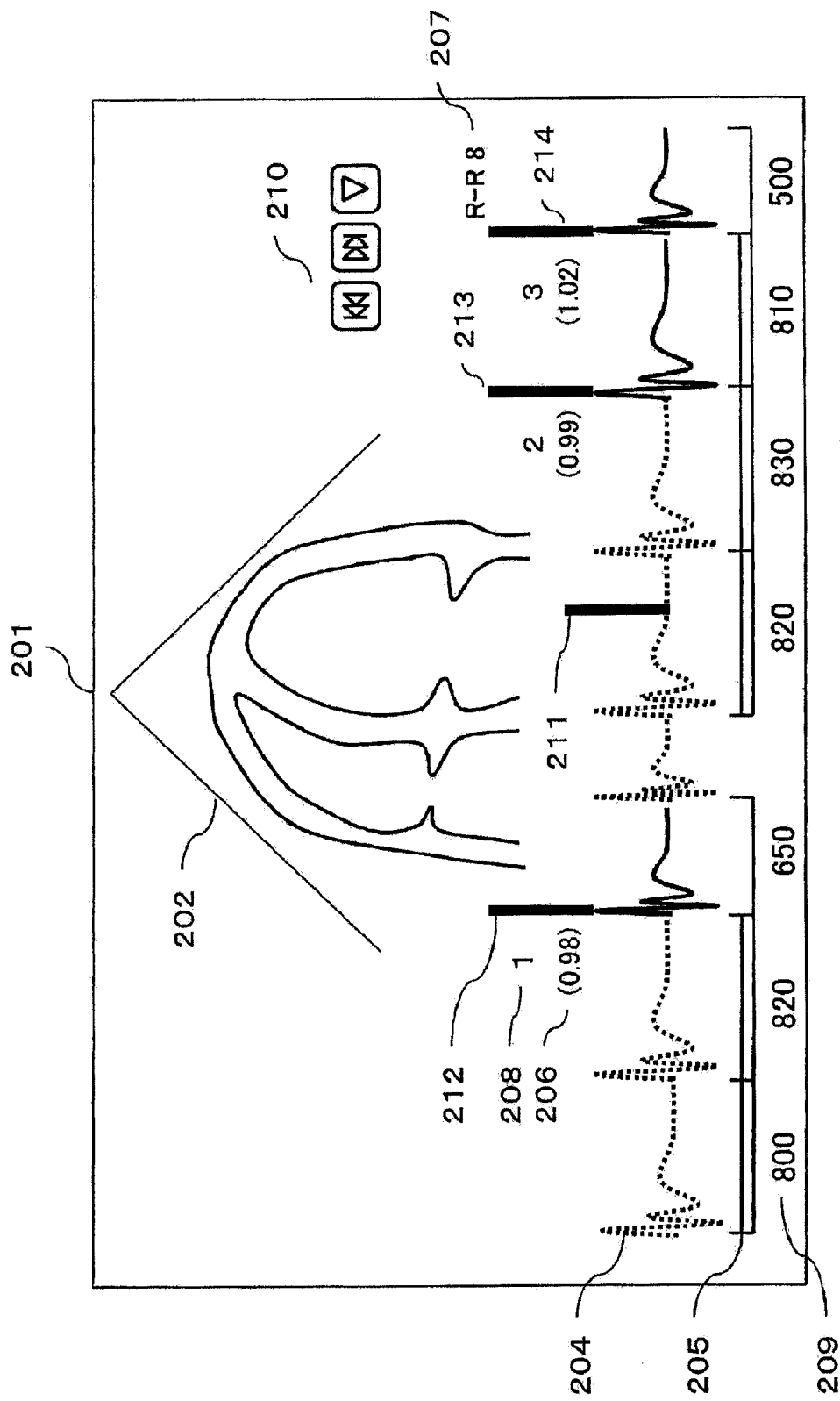
FIG. 10 A diagram for describing the operation of jumping of a time phase bar in Embodiment 3 of the method of retrieving and displaying the heart function test period in the present invention.

FIG. 10 shows an example of the display image of the data for electrocardiographically analyzing the functions in the present embodiment. As shown, a jump button 210 for jumping the time phase bar is provided on the screen, for example. A rightward arrow of the button 210 is set to perform a rightward jump (to an advanced time phase) from the current time phase, and a leftward arrow is set to perform a leftward jump (to a past time phase) from the current time phase. For example, when the current time phase is located at the position of a time phase bar 211, selection and pressing of the leftward arrow of the jump button 210 causes jumping from the current time phase to the past R wave time phase in the first test period having the first serial number and moves the time phase bar 212 to that time phase position. This changes the ultrasonic image 202 into an image at the time phase of the time phase bar 212. Although not shown, Doppler measurement values and the like can be displayed at the time phase of the time phase bar 212. In contrast, selection and pressing of the rightward arrow of the jump button 210 causes jumping of the time phase bar 213 from the current time phase to the advanced R wave time phase in the test period having the second serial number. When the rightward arrow of the jump button 210 is again selected and pressed, further advancement is made to cause jumping of the time phase bar 214 to the R wave time phase in the test period having the third serial number.

A downward arrow of the jump button 210 is set to move the time phase bar in the order of the evaluation value 206. When the downward arrow is pressed once, the test period having the higher evaluation value 206 can be switched to the test periods having the lower evaluation values in descending order to jump to a desired test period.

Since the serial number is given to the test period, the serial number of the test period to which the jumping is to be performed is input through the input section 7 to allow jumping to the R wave time phase in the test period having the input serial number.

Instead of the jump button 210, the track ball provided for the input section 7 can be used. In this case, setting is performed such that rotation of the track ball to the left causes jumping to the past R wave time phase in the test period and rotation of the track ball to the right causes jumping to the advanced R wave time phase in the test period. The present invention is not limited to the track ball, and any input device can be used as long as the position can be specified.

According to Embodiment 3 described above, only the R wave time phase in the test period can be moved, so that the tester can easily jump to access the desired test period without searching for the desired test period while checking the image. Since the jumping can be made in descending order of evaluation value, the tester can easily access the test period associated with the conforming period having the highest evaluation value. As a result, immediate transition can be made to the measurement operation or the like in the desired test period to contribute to the improvement of the test efficiency.

Embodiment 4

Figure 11:
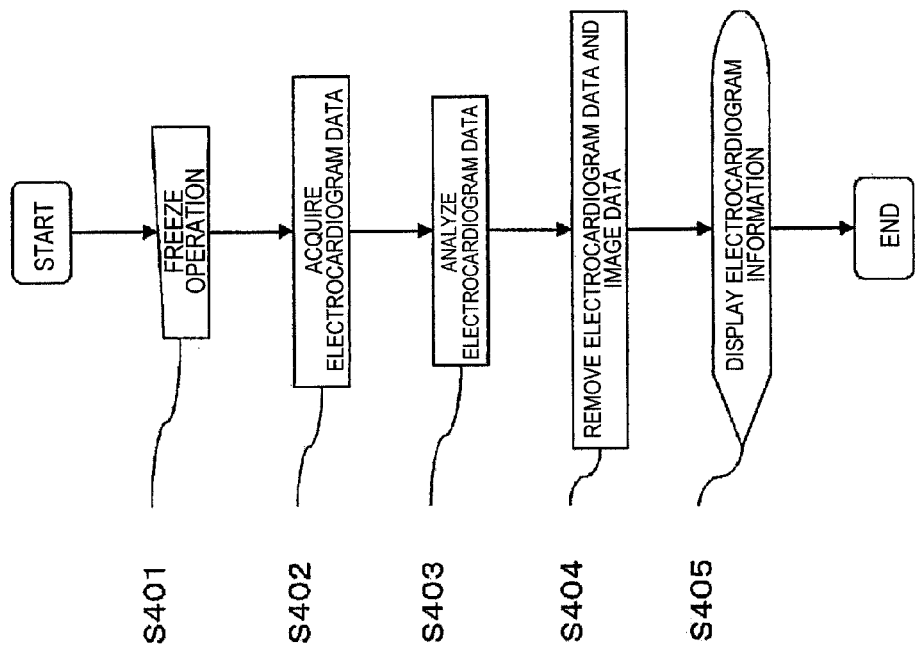
FIG. 11 A flow chart of Embodiment 4 of the method of retrieving and displaying the heart function test period in the present invention.

Embodiment 4 is an example which involves removing data for measuring heart functions, which is electrocardiogram data and ultrasonic image data other than those in the conforming periods and the test periods retrieved in Embodiments 1 and 2, to perform edits to provide only the required heart function measurement data. FIG. 11 shows a flow chart of the present embodiment. In FIG. 11, steps S401 to S403 are identical to steps S102 to S104 in Embodiment 1. In the present embodiment, after the completion of the analysis of the electrocardiogram data at step S403, the electrocardiogram data and the ultrasonic image data are edited and that data is displayed at step S405.

Figure 12:
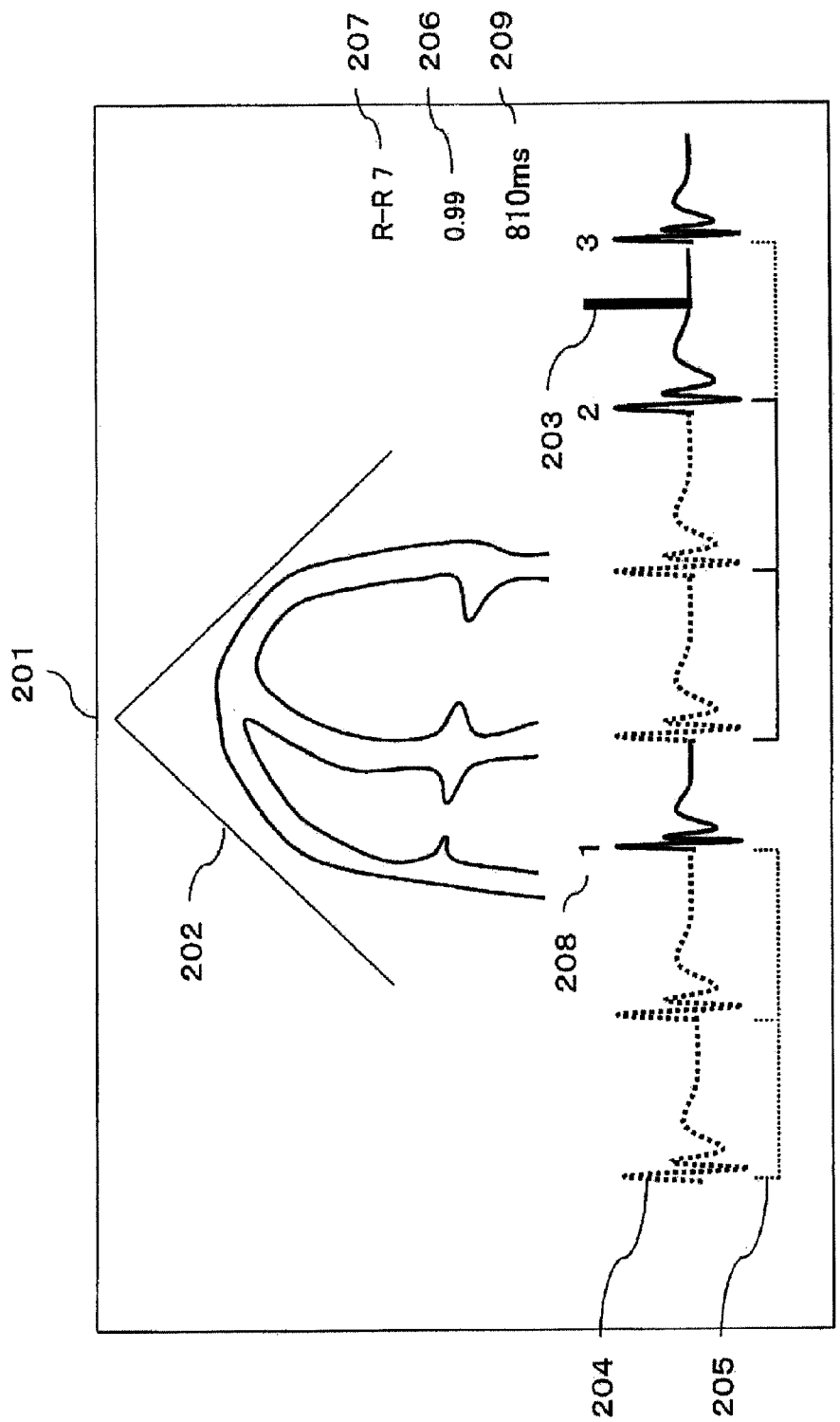
FIG. 12 An exemplary display screen in which display items representing the result of retrieval of the heart function test period are simplified.

FIG. 12 shows an example of the display image in the present embodiment. FIG. 12 shows the data for measuring the heart functions edited by cutting the portion not corresponding to any conforming period or any test period in FIG. 7 and combining the portions before and after the cut portion. Specifically, the R-R period at the fourth beat in FIG. 7 is removed and the portions before and after that period are combined. The ultrasonic image data is also provided by removing that R-R period and combining the portions before and after that removed portion.

Instead of FIG. 12, when the data for measuring the heart functions is reproduced without cutting the portion not corresponding to any conforming period or any test period, the data of the portion not corresponding to any conforming period or any test period can be assumed to be absent and can be skipped in the reproduction.

As described above, according to Embodiment 4, the data not relating to any conforming period or any test period, that is, the unnecessary data in the test of arrhythmia is removed or skipped out of the acquired data, so that the immediate access can be made to the target test period. Since the unnecessary data is removed, only the useful data is taken into the memory to improve the efficiency of data collection. Thus, immediate transition can be made to the measurement operation or the like in the desired test period, so that the test efficiency is improved.

DESCRIPTION OF REFERENCE NUMERALS AND SIGNS

1 ULTRASONIC DIAGNOSTIC APPARATUS, 2 OBJECT, 3 ULTRASONIC PROBE, 4 ULTRASONIC TRANSMITTING/RECEIVING SECTION, 5 ULTRASONIC IMAGE PRODUCING SECTION, 6 STORAGE SECTION, 7 INPUT SECTION, 8 OUTPUT/DISPLAY SECTION, 9 BIO-SIGNAL ACQUIRING SECTION, 10 BIO-SIGNAL ANALYZING SECTION, 11 MEASURING AND COMPUTING SECTION, 12 CONTROL SECTION

The invention claimed is:

1. An ultrasonic diagnostic apparatus comprising:
an ultrasonic image producing section that transmits ultrasonic waves to an object with an ultrasonic probe and produces ultrasonic image data based on a ultrasonic reception signal;
a heart function measuring and computing section that determines heart function measurement data using the ultrasonic reception signal;
a bio-signal acquiring section that acquires a bio-signal periodically changing due to motions of a heart of the object;
a display section that displays the ultrasonic image data, the heart function measurement data, and an image of the bio-signal, wherein the bio-signal includes an electrocardiogram;
a control section that controls each of the sections; and
a bio-signal analyzing section, communicatively connected to the bio-signal acquiring section, that:
detects a plurality of specific waves and obtains specific waves-specific waves intervals,
evaluates irregularity of specific waves by a result obtained by judging whether a ratio of consecutive two or more specific waves-specific waves intervals is in a predetermined range, and
sets non-conforming period or conforming period by the results of the evaluation.

2. The ultrasonic diagnostic apparatus according to claim 1, wherein the control section causes the display section to output and display a signal waveform of the bio-signal, a test period, and a content of the evaluation in a time phase of the bio-signal associated by the bio-signal analyzing section.

3. The ultrasonic diagnostic apparatus according to claim 1, wherein the control section causes the display section to highlight a signal waveform of the bio-signal in a segment corresponding to a test period.

4. The ultrasonic diagnostic apparatus according to claim 1, further comprising a storage section that stores ultrasonic measurement data including the ultrasonic image data, the bio-signal, and the heart function measurement data,
wherein the control section causes the display section to display the ultrasonic measurement data associated with a test period and a signal waveform of the bio-signal.

5. The ultrasonic diagnostic apparatus according to claim 4, wherein the bio-signal acquiring section acquires data of the bio-signal stored in the storage section and inputs the acquired data to the bio-signal analyzing section when a freeze instruction is input through the input section, or inputs the bio-signal acquired in real time to the bio-signal analyzing section when the freeze instruction is not input through the input section.

6. The ultrasonic diagnostic apparatus according to claim 4, wherein the control section retrieves a test period stored in the storage section, jumps to the retrieved test period, and causes the display section to display the bio-signal stored in the storage section in response to an instruction input through the input section.

7. The ultrasonic diagnostic apparatus according to claim 1, wherein the bio-signal analyzing section performs the evaluation to determine whether a heart function is stable based on whether a difference or a ratio between time intervals between particular signal waveforms adjacent in a number of successive periods set on a time axis satisfies a set threshold value, and/or matching between adjacent particular signal waveforms satisfies a set threshold value, and a value of the difference or the ratio between the time intervals or a value of the matching between the particular signal waveforms is displayed as the content of the evaluation on the display section.

8. The ultrasonic diagnostic apparatus according to claim 1, wherein, in reproducing and displaying the bio-signal stored in the storage section in the display section, the control section edits the bio-signal to include only a test period or only the test period and only a preset number of successive periods preceding to the test period and causes the display section to display the edited signal.

9. The ultrasonic diagnostic apparatus according to claim 1, wherein, when a test period comprises a plurality of test periods, the control section causes the display section to display a serial number of each of the plurality of test periods.

10. The ultrasonic diagnostic apparatus according to claim 9, wherein, when the serial number of the test period is input through the input section, the control section searches the storage section to retrieve the test period associated with the serial number, jumps to the retrieved test period, and causes the display section to display the bio-signal stored in the storage section.

11. The ultrasonic diagnostic apparatus according to claim 1, wherein the specific waves include R waves.

* * * * *